(12) United States Patent
Iimura et al.

(10) Patent No.: US 10,125,242 B2
(45) Date of Patent: Nov. 13, 2018

(54) ORGANOSILICON COMPOUND, CURABLE SILICONE COMPOSITION, AND SEMICONDUCTOR DEVICE

(71) Applicant: Dow Corning Toray Co., Ltd., Tokyo (JP)

(72) Inventors: Tomohiro Iimura, Ichihara (JP); Nohno Toda, Ichihara (JP); Sawako Inagaki, Ichihara (JP); Yusuke Miyamoto, Ichihara (JP); Haruhiko Furukawa, Ichihara (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 183 days.

(21) Appl. No.: 15/315,067

(22) PCT Filed: May 28, 2015

(86) PCT No.: PCT/JP2015/002699
§ 371 (c)(1),
(2) Date: Nov. 30, 2016

(87) PCT Pub. No.: WO2015/182143
PCT Pub. Date: Dec. 3, 2015

(65) Prior Publication Data
US 2017/0190878 A1 Jul. 6, 2017

(30) Foreign Application Priority Data
May 30, 2014 (JP) .................... 2014-112614

(51) Int. Cl.
| | | |
|---|---|---|
| C08K 5/54 | (2006.01) | |
| C07F 7/08 | (2006.01) | |
| H01L 23/29 | (2006.01) | |
| C07F 7/18 | (2006.01) | |
| C08K 5/549 | (2006.01) | |
| H01L 23/31 | (2006.01) | |
| H01L 33/56 | (2010.01) | |

(52) U.S. Cl.
CPC ............ C08K 5/549 (2013.01); C07F 7/08 (2013.01); C07F 7/18 (2013.01); C07F 7/184 (2013.01); C07F 7/1836 (2013.01); H01L 23/29 (2013.01); H01L 23/31 (2013.01); H01L 33/56 (2013.01); H01L 2224/32245 (2013.01); H01L 2224/48091 (2013.01); H01L 2224/48247 (2013.01); H01L 2224/73265 (2013.01)

(58) Field of Classification Search
CPC ... C08K 5/549; C07F 7/08; C07F 7/18; C07F 7/1836; C07F 7/184; H01L 23/29; H01L 23/31; H01L 33/56; H01L 2224/48091; H01L 2224/48247; H01L 2224/73265
USPC ....................................................... 524/107
See application file for complete search history.

(56) References Cited

U.S. PATENT DOCUMENTS

| | | | | |
|---|---|---|---|---|
| 6,303,811 | B1 * | 10/2001 | Krahnke | .............. C07F 7/21 556/436 |
| 6,784,300 | B2 * | 8/2004 | Cetin | ............. C08G 59/3254 430/1 |
| 7,332,249 | B2 | 2/2008 | Cetin et al. | |
| 8,168,737 | B2 * | 5/2012 | Alvarez | .............. C08G 77/14 525/476 |
| 8,373,196 | B2 * | 2/2013 | Kashiwagi | ............. H01L 24/48 257/100 |
| 2002/0006823 | A1 * | 1/2002 | Horio | ................. A63F 13/06 463/36 |
| 2002/0068223 | A1 | 6/2002 | Cetin et al. | |
| 2004/0249181 | A1 | 12/2004 | Cetin et al. | |
| 2007/0293637 | A1 | 12/2007 | Cetin et al. | |
| 2010/0069523 | A1 * | 3/2010 | Alvarez | .............. C08G 77/14 522/148 |
| 2010/0224906 | A1 * | 9/2010 | Kashiwagi | ............. H01L 24/48 257/100 |
| 2010/0280260 | A1 | 11/2010 | Cetin et al. | |
| 2015/0252220 | A1 * | 9/2015 | Okawa | ................. C08K 3/22 252/301.36 |
| 2015/0274895 | A1 * | 10/2015 | Okawa | ................. H01L 33/56 523/210 |

FOREIGN PATENT DOCUMENTS

| | | |
|---|---|---|
| CN | 104603192 A | 5/2015 |
| CN | 104640946 A | 5/2015 |
| EP | 0853101 A1 | 7/1998 |
| EP | 1 013 657 A2 | 6/2000 |
| EP | 1 317 498 B1 | 6/2006 |
| EP | 2 097 471 A | 7/2008 |
| EP | 2 226 360 A1 | 9/2010 |
| JP | 2000-191672 A | 7/2000 |

(Continued)

OTHER PUBLICATIONS

International Search Report for Application No. PCT/JP2015/002699 dated Aug. 11, 2015, 2 pages.

(Continued)

Primary Examiner — Michael Bernshteyn
(74) Attorney, Agent, or Firm — Howard & Howard Attorneys PLLC

(57) ABSTRACT

An organosilicon compound represented by the general formula, a hydrosilylation-curable silicone composition containing the compound as an adhesion promoter, and a semiconductor device having a semiconductor element sealed with a cured product of the composition. To provide a novel organosilicon compound, a curable silicone composition that contains the organosilicon compound as an adhesion promoter, has excellent initial adhesion and adhesion durability to a base material such as an organic resin, and forms a cured product having high light transmittance, and a highly reliable semiconductor device produced using this composition.

19 Claims, 1 Drawing Sheet

(56) References Cited

FOREIGN PATENT DOCUMENTS

| | | |
|---|---|---|
| JP | 2004-507513 A | 3/2004 |
| JP | 2010-513664 A | 4/2010 |
| JP | 2010-229402 A | 10/2010 |
| JP | 2014-062198 A | 4/2014 |
| JP | 2014-077177 A | 5/2014 |
| WO | WO 02/19040 A2 | 3/2002 |
| WO | WO 2008/088523 A1 | 7/2008 |
| WO | WO 2014/046308 A1 | 3/2014 |
| WO | WO 2014/046309 A1 | 3/2014 |

OTHER PUBLICATIONS

English language abstract for CN 104603192 extracted from espacenet.com database on Jan. 19, 2017, 1 page.

English language abstract for CN 104640946 extracted from espacenet.com database on Jan. 19, 2017, 1 page.

English language abstract not found for EP 2 097 471; however, see corresponding international publication WO 2008/088523 extracted from espacenet.com database on Jan. 19, 2017.

English language abstract for JP 2000-191672 extracted from espacenet.com database on Jan. 19, 2017, 2 pages.

English language abstract not found for JP 2004-507513; however, see English language equivalent U.S. Pat. No. 7,332,249. Original document extracted from espacenet.com database on Jan. 19, 2017, 159 pages.

English language abstract not found for JP 2010-513664; however, see English language equivalent U.S. Pat. No. 8,168,737. Original document extracted from espacenet.com database on Jan. 19, 2017, 15 pages.

English language abstract for JP 2010-229402 extracted from espacenet.com database on Jan. 19, 2017, 2 pages.

English language abstract for JP 2014-062198 extracted from espacenet.com database on Jan. 19, 2017, 1 page.

English language abstract for JP 2014-077117 extracted from espacenet.com database on Jan. 19, 2017, 2 pages.

\* cited by examiner

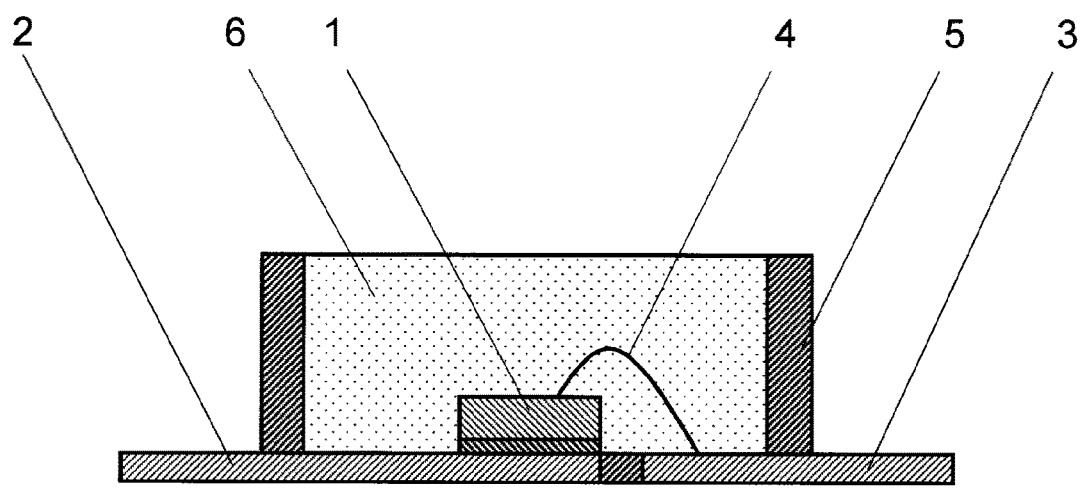

ORGANOSILICON COMPOUND, CURABLE SILICONE COMPOSITION, AND SEMICONDUCTOR DEVICE

CROSS-REFERENCE TO RELATED APPLICATIONS

This application is the National Stage of International Patent Application No. PCT/JP2015/002699, filed on May 28, 2015, which claims priority to and all the advantages of Japanese Patent Application No. 2014-112614, filed on May 30, 2014, the content of which is incorporated herein by reference.

TECHNICAL FIELD

The present invention relates to a novel organosilicon compound, a curable silicone composition containing the organosilicon compound as an adhesion promoter, and a semiconductor device produced using the composition.

BACKGROUND ART

A curable silicone composition to be cured by a hydrosilylation reaction generally has low adhesion. Therefore, when adhesion is required, the curable silicone composition should contain an adhesion promoter. For example, Patent Document 1 discloses a curable silicone composition contains an adhesion promoter which is a cyclic siloxane or linear siloxane having an alkenyl group, and an alkoxy group or a glycidoxypropyl group that are bonded to silicon atoms.

However, such a curable silicone composition has problems in which initial adhesion and adhesion durability are insufficient with respect to a metal or an organic resin, particularly, a thermoplastic resin to be bonded to a highly polar group, under contact during curing.

CITATION LIST

Patent Literature

Patent Document 1: Japanese Unexamined Patent Application Publication No. 2010-229402A

SUMMARY OF INVENTION

Technical Problem

An object of the present invention is to provide a novel organosilicon compound, a curable silicone composition that contains the organosilicon compound as an adhesion promoter, has excellent initial adhesion and adhesion durability to a base material such as a metal and an organic resin, and forms a cured product having high light transmittance, and a highly reliable semiconductor device produced using this composition.

Solution to Problem

An organosilicon compound of the present invention is represented by the general formula:

[Chemical Formula 1]

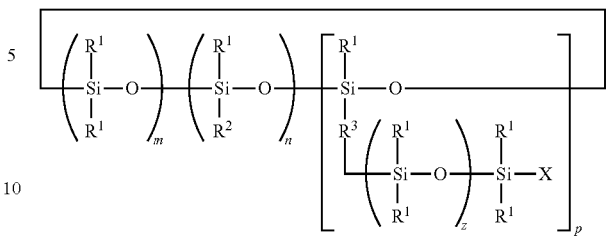

wherein, $R^1$ are the same or different monovalent hydrocarbon groups having from 1 to 12 carbons and no aliphatic unsaturated bond; $R^2$ is an alkenyl group having from 2 to 12 carbons; $R^3$ is an alkylene group having from 2 to 12 carbons; X is at least one group selected from the group consisting of an alkoxysilylalkyl group, a glycidoxyalkyl group, an epoxycycloalkylalkyl group, an epoxyalkyl group, and a carboxylic acid anhydride residue-containing alkyl group; m is an integer of 0 or greater, n is an integer of 1 or greater, and p is an integer of 1 or greater, provided that the sum of m, n, and p is an integer of from 3 to 50; and z is an integer of from 1 to 50.

Another organosilicon compound of the present invention is represented by the general formula:

[Chemical Formula 2]

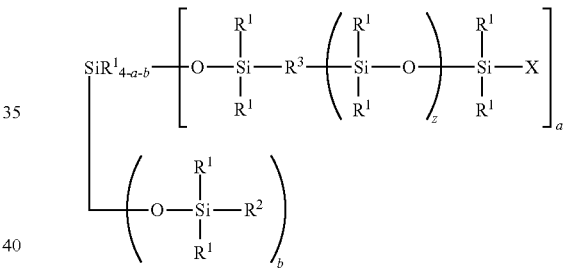

wherein, $R^1$ are the same or different monovalent hydrocarbon groups having from 1 to 12 carbons and no aliphatic unsaturated bond; $R^2$ is an alkenyl group having from 2 to 12 carbons; $R^3$ is an alkylene group having from 2 to 12 carbons; X is at least one group selected from the group consisting of an alkoxysilylalkyl group, a glycidoxyalkyl group, an epoxycycloalkylalkyl group, an epoxyalkyl group, and a carboxylic acid anhydride residue-containing alkyl group; a is an integer of from 1 to 3 and b is an integer of from 1 to 3, provided that the sum of a and b is an integer of from 2 to 4; and z is an integer of from 1 to 50.

A curable silicone composition of the present invention contains the organosilicon compound as an adhesion promoter. The curable silicone composition is preferably cured by a hydrosilylation reaction, and more preferably comprises:

(A) 100 parts by mass of an organopolysiloxane having at least two alkenyl groups in a molecule;

(B) an organohydrogenpolysiloxane having at least two silicon atom-bonded hydrogen atoms in a molecule, in an amount such that 0.1 to 10.0 mol of silicon atom-bonded hydrogen atom is provided relative to 1 mol of all alkenyl groups in components (A) and (C);

(C) 0.01 to 50 parts by mass of adhesion promoter containing of the organosilicon compound described above; and (D) a hydrosilylation reaction catalyst, in an amount sufficient to promote curing of the present composition.

A semiconductor device of the present invention has a semiconductor element encapsulated with a cured product of the curable silicone composition described above, and preferably, the semiconductor element is a light emitting element.

Effects of Invention

The organosilicon compound of the present invention is a novel compound and can impart excellent adhesion to a curable silicone composition. The curable silicone composition of the present invention is characterized by high refractive index, light transmittance, and adhesiveness to a base material of a cured product. The semiconductor device of the present invention has excellent reliability since the semiconductor element is coated with the cured product of the composition.

BRIEF DESCRIPTION OF THE DRAWINGS

FIG. 1 is a cross-sectional view of an LED that is an example of a semiconductor device of the present invention.

DETAILED DESCRIPTION OF THE INVENTION

The organosilicon compound of the present invention will be first described in detail.

The organosilicon compound of the present invention is represented by the general formula:

[Chemical Formula 3]

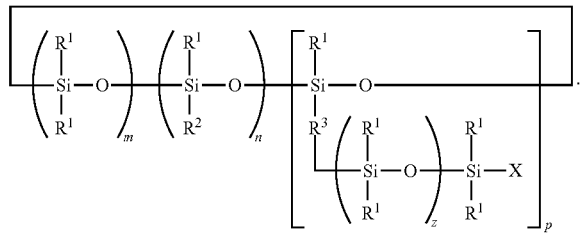

In the formula, $R^1$ are the same or different monovalent hydrocarbon groups having from 1 to 12 carbons and no aliphatic unsaturated bond. Specific examples thereof include alkyl groups such as a methyl group, an ethyl group, a propyl group, a butyl group, a pentyl group, and a hexyl group; aryl groups such as a phenyl group, a tolyl group, a xylyl group, and a naphthyl group; aralkyl groups such as a benzyl group and a phenethyl group; and halogenated alkyl groups such as a 3-chloropropyl group and a 3,3,3-trifluoropropyl group. A methyl group and a phenyl group are preferred.

In the formula, $R^2$ is an alkenyl group having from 2 to 12 carbons. Specific examples thereof include a vinyl group, an allyl group, a butenyl group, a pentenyl group, a hexenyl group, a heptenyl group, an octenyl group, a nonenyl group, a decenyl group, an undecenyl group, and a dodecenyl group. A vinyl group is preferred.

In the formula, $R^3$ is an alkylene group having from 2 to 12 carbons. Specific examples thereof include an ethylene group, a propylene group, a butylene group, a pentylene group, a hexylene group, a heptylene group, an octylene group, and a nonylene group. An ethylene group and a propylene group are preferred.

In the formula, X is at least one group selected from the group consisting of an alkoxysilylalkyl group, a glycidoxyalkyl group, an epoxycycloalkylalkyl group, an epoxyalkyl group, and a carboxylic acid anhydride residue-containing alkyl group. Examples of the alkoxysilylalkyl group include a trimethoxysilylethyl group, a methyldimethoxysilylethyl group, a triethoxysilylethyl group, a triisopropoxysilylethyl group, a trimethoxysilylpropyl group, and a trimethoxysilylbutyl group. Examples of the glycidoxyalkyl group include a 2-glycidoxyethyl group, a 3-glycidoxypropyl group, and a 4-glycidoxybutyl group. Examples of the epoxycycloalkylalkyl group include 2-(3,4-epoxycyclohexyl)-ethyl group and 3-(3,4-epoxycyclohexyl)-propyl group. Examples of the epoxyalkyl group include a 3,4-epoxybutyl group, and a 7,8-epoxyoctyl group. Examples of the carboxylic acid anhydride residue-containing alkyl group include a group represented by the general formula:

[Chemical Formula 4]

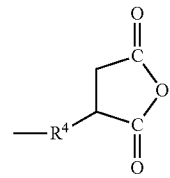

a group represented by the general formula:

[Chemical Formula 5]

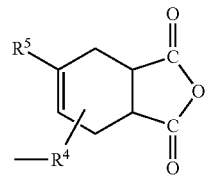

a group represented by the general formula:

[Chemical Formula 6]

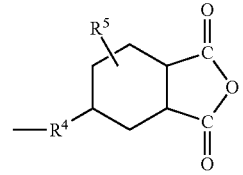

a group represented by the general formula:

[Chemical Formula 7]

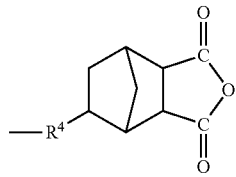

and a group represented by the general formula:

[Chemical Formula 8]

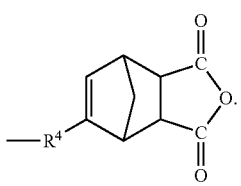

In the formulae, $R^4$ is an alkylene group having from 2 to 12 carbons. Examples of the alkylene group of $R^4$ are the same as the groups described in $R^3$. In the formulae, $R^5$ is a hydrogen atom or alkyl groups having from 1 to 12 carbons. Examples of the alkyl groups of $R^5$ are the same as the groups described for $R^1$.

In the formula, m is an integer of 0 or greater, n is an integer of 1 or greater, and p is an integer of 1 or greater, provided that the sum of m, n, and p is an integer of from 3 to 50. In the formula, z is an integer of from 1 to 50, and preferably an integer of from 1 to 5. In particular, an organosiloxane in which m is 0, n is an integer of 2 or greater, p is an integer of 2 or greater, and z is 1 is preferred.

Examples of such an organosilicon compound include the following compounds.

[Chemical Formula 9]

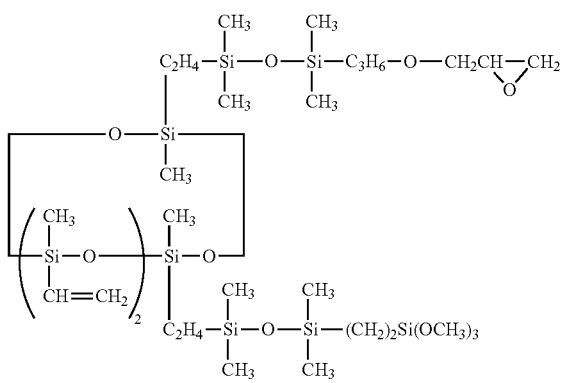

[Chemical Formula 10]

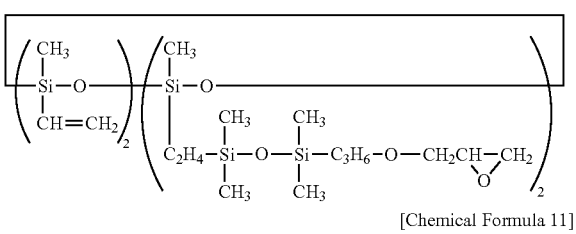

[Chemical Formula 11]

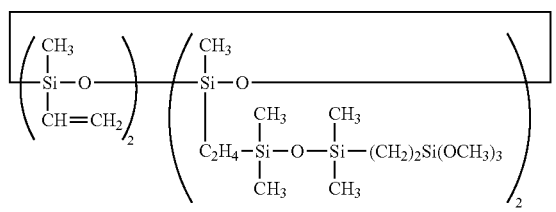

The other organosilicon compound of the present invention is represented by the general formula:

[Chemical Formula 12]

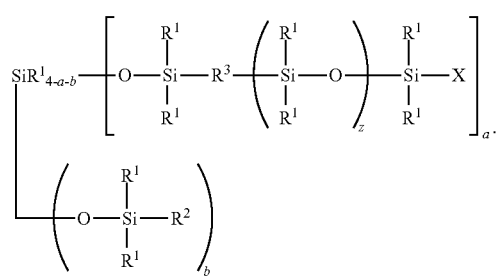

In the formula, $R^1$ are the same or different monovalent hydrocarbon groups having from 1 to 12 carbons and no aliphatic unsaturated bond, and examples thereof are the same as the groups described above. In the formula, $R^2$ is an alkenyl group having from 2 to 12 carbons, and examples thereof are the same as the groups described above. In the formula, $R^3$ is an alkylene group having from 2 to 12 carbons, and examples thereof are the same as the groups described above. In the formula, X is at least one group selected from the group consisting of an alkoxysilylalkyl group, a glycidoxyalkyl group, an epoxycycloalkylalkyl group, an epoxyalkyl group, and a carboxylic acid anhydride residue-containing alkyl group, and examples thereof are the same as the groups described above.

In the formula, a is an integer of from 1 to 3, and b is an integer of from 1 to 3, provided that the sum of a and b is an integer of from 2 to 4. In the formula, z is an integer of from 1 to 50, and preferably an integer of from 1 to 5. In particular, an organosiloxane in which a is an integer of from 1 to 2, b is an integer of from 2 to 3, and z is 1 is preferred.

Examples of such an organosilicon compound include the following compounds.

[Chemical Formula 13]

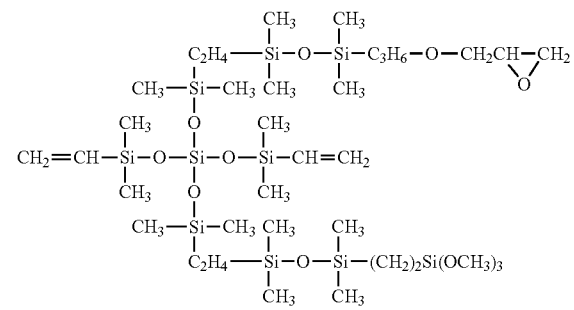

[Chemical Formula 14]

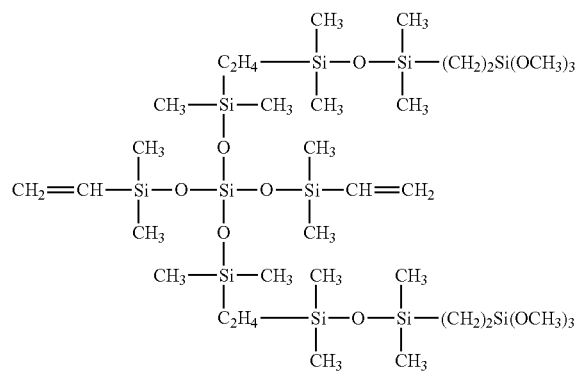

[Chemical Formula 15]

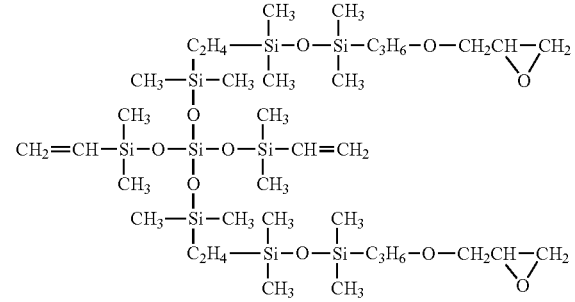

Examples of a method for preparing such an organosilicon compound include a preparation method by a partial addition reaction of a cyclic siloxane represented by the general formula:

[Chemical Formula 16]

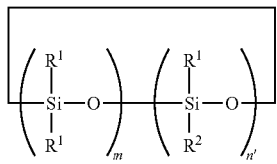

or a chain siloxane represented by the general formula:

[Chemical Formula 17]

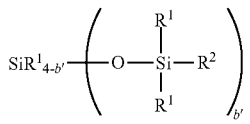

with a silicon atom-bonded hydrogen atom-containing siloxane represented by the general formula:

[Chemical Formula 18]

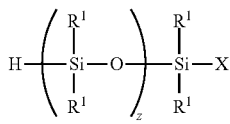

in the presence of a hydrosilylation reaction catalyst.

In the cyclic siloxane, $R^1$, $R^2$, and m in the formula are as described above. In the formula, n' is an integer of 2 or greater. Provided that the sum of m and n' is an integer of from 3 to 50. Examples of such a cyclic siloxane include cyclic methylvinylsiloxane, cyclic methylallylsiloxane, and a cyclic dimethylsiloxane-methylvinylsiloxane copolymer.

In the chain siloxane, $R^1$ and $R^2$ in the formula are as described above. In the formula, b' is an integer of from 2 to 4. Examples of such a linear siloxane include tetrakis(dimethylvinylsiloxy)silane and methyltris(dimethylvinylsiloxy)silane.

In the silicon atom-bonded hydrogen atom-containing siloxane, $R^1$, X, and z are as described above. Examples of such a silicon atom-bonded hydrogen atom-containing siloxane include the following compounds.

[Chemical Formula 19]

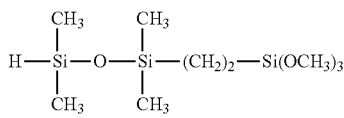

[Chemical Formula 20]

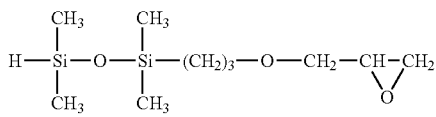

[Chemical Formula 21]

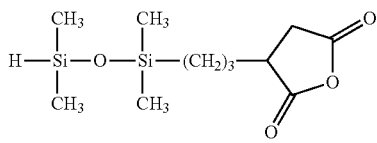

Examples of the hydrosilylation reaction catalyst used in the above-described preparation method include a platinum-based catalyst, a rhodium-based catalyst, and a palladium-based catalyst. A platinum-based catalyst is particularly preferred. Examples of the platinum-based catalyst include platinum-based compounds, such as platinum fine powder, platinum black, platinum-supporting silica fine powder, platinum-supporting activated carbon, chloroplatinic acid, alcohol solutions of chloroplatinic acid, olefin complexes of platinum, and alkenylsiloxane complexes of platinum.

Further, an organic solvent may be used in the preparation method described above. Examples of usable organic solvent include ethers, ketones, acetates, aromatic or aliphatic hydrocarbons, and γ-butyrolactone, and mixtures of two or more types of these solvents. Preferable examples of the organic solvent include propylene glycol monomethyl ether, propylene glycol monomethyl ether acetate, propylene glycol monoethyl ether, propylene glycol monopropyl ether, propylene glycol monobutyl ether, propylene glycol mono-tert-butyl ether, γ-butyrolactone, toluene, and xylene.

In the preparation method, it is preferable that silicon atom-bonded hydrogen atoms in the silicon atom-bonded hydrogen atom-containing siloxane be reacted in an amount of less than 1 mol, and specifically, in an amount within the range of from 0.25 to 0.75 mol, relative to 1 mol of alkenyl groups in the cyclic siloxane or the chain siloxane.

Such an organosilicon compound is a novel compound having a siloxane bond and a silalkylene bond, and can be used as an adhesion promoter for a curable silicone composition, a surface treatment agent for an inorganic powder, or the like.

Next, the curable silicone composition of the present invention will be described in detail. The curable silicone composition of the present invention contains the organosilicon compound described above as an adhesion promoter. A curing mechanism of the curable silicone composition is not limited, and examples thereof include a hydrosilylation reaction, a condensation reaction, and a radical reaction. A hydrosilylation reaction is preferred. Specifically, it is preferable that the curable silicone composition to be cured by this hydrosilylation reaction comprises:

(A) 100 parts by mass of organopolysiloxane having at least two alkenyl groups in a molecule;
(B) an organohydrogenpolysiloxane having at least two silicon atom-bonded hydrogen atoms in a molecule, in an amount such that 0.1 to 10.0 mol of silicon atom-bonded hydrogen atom is provided relative to 1 mol of all alkenyl groups in components (A) and (C);
(C) 0.01 to 50 parts by mass of adhesion promoter containing the organosilicon compound; and
(D) a hydrosilylation reaction catalyst.

Component (A) is the base compound of the present composition and is an organopolysiloxane having at least two alkenyl groups in a molecule. Examples of the alkenyl groups include alkenyl groups having from 2 to 12 carbons such as a vinyl group, an allyl group, a butenyl group, a pentenyl group, a hexenyl group, a heptenyl group, an octenyl group, a nonenyl group, a decenyl group, an undecenyl group, and a dodecenyl group, and a vinyl group is preferred. Examples of a group bonded to the silicon atom other than the alkenyl groups in component (A) include alkyl groups having from 1 to 12 carbons such as a methyl group, an ethyl group, a propyl group, an isopropyl group, a butyl group, an isobutyl group, a tert-butyl group, a pentyl group, a neopentyl group, a hexyl group, a cyclohexyl group, a heptyl group, an octyl group, a nonyl group, a decyl group, an undecyl group, and a dodecyl group; aryl groups having from 6 to 20 carbons such as a phenyl group, a tolyl group, a xylyl group, and a naphthyl group; aralkyl groups having from 7 to 20 carbons such as a benzyl group, a phenethyl group, and a phenylpropyl group; and these groups in which a part or all of the hydrogen atoms is substituted with a halogen atom such as a fluorine atom, a chloride atom, and a bromine atom. The silicon atom in component (A) may be bonded to a hydroxyl group or an alkoxy group such as a methoxy group and an ethoxy group in a small amount as long as the object of the present invention is not impaired.

The molecular structure of component (A) is not particularly limited, and examples thereof include linear, partially branched linear, cyclic, and three-dimensional network structures. Component (A) may be one type of organopolysiloxane having the molecular structures or a mixture of two or more types of organopolysiloxane having the molecular structures.

The state of component (A) at 25° C. is not particularly limited, and examples thereof include a liquid and a solid. When component (A) is a liquid at 25° C., the viscosity at 25° C. is preferably in the range of from 1 to 1,000,000 mPa·s, and particularly preferably in the range of from 10 to 1,000,000 mPa·s. The viscosity may be, for example, determined by measurement using a B type viscometer in accordance with JIS K7117-1.

Examples of such component (A) include a dimethylpolysiloxane having both molecular terminals capped with dimethylvinylsiloxy groups, a dimethylsiloxane-methylvinylsiloxane copolymer having both molecular terminals capped with dimethylvinylsiloxy groups, a dimethylsiloxane-methylphenylsiloxane copolymer having both molecular terminals capped with dimethylvinylsiloxy groups, a methylphenylpolysiloxane having both molecular terminals capped with dimethylvinylsiloxy groups, a dimethylsiloxane-methylvinylsiloxane copolymer having both molecular terminals capped with trimethylsiloxy groups, a dimethylsiloxane-methylvinylsiloxane-methylphenylsiloxane copolymer having both molecular terminals capped with trimethylsiloxy groups, a copolymer including a $(CH_3)_3SiO_{1/2}$ unit, a $(CH_3)_2(CH_2=CH)SiO_{1/2}$ unit, and a $SiO_{4/2}$ unit, a copolymer including a $(CH_3)_2(CH_2=CH)SiO_{1/2}$ unit and a $SiO_{4/2}$ unit, and the following organopolysiloxanes. Note that, in the formulae, Me, Vi, and Ph represent a methyl group, a vinyl group, and a phenyl group, respectively, and x and x' are each an integer of from 1 to 100.

$ViMe_2SiO(Me_2SiO)_xSiMe_2Vi$
$ViPhMeSiO(Me_2SiO)_xSiMePhVi$
$ViPh_2SiO(Me_2SiO)_xSiPh_2Vi$
$ViMe_2SiO(Me_2SiO)_x(Ph_2SiO)_{x'}SiMe_2Vi$
$ViPhMeSiO(Me_2SiO)_x(Ph_2SiO)_{x'}SiPhMeVi$
$ViPh_2SiO(Me_2SiO)_x(Ph_2SiO)_{x'}SiPh_2Vi$
$ViMe_2SiO(MePhSiO)_xSiMe_2Vi$
$MePhViSiO(MePhSiO)_xSiMePhVi$
$Ph_2ViSiO(MePhSiO)_xSiPh_2Vi$
$ViMe_2SiO(Ph_2SiO)_x(PhMeSiO)_xSiMe_2Vi$
$ViPhMeSiO(Ph_2SiO)_x(PhMeSiO)_xSiPhMeVi$
$ViPh_2SiO(Ph_2SiO)_x(PhMeSiO)_xPh_2Vi$

Component (B) is a crosslinking agent of the present composition and is an organohydrogenpolysiloxane having at least two silicon atom-bonded hydrogen atoms in a molecule. Examples of the molecular structure of component (B) include linear, partially branched linear, branched chain, cyclic, and dendritic structures, and linear, partially branched linear, and dendritic structures are preferred. The bonding positions of the silicon atom-bonded hydrogen atoms in component (B) are not limited, and examples thereof include terminals and/or side chains of molecular chain. Examples of silicon atom-bonded groups other than hydrogen atoms in component (B) include alkyl groups such as a methyl group, an ethyl group, and a propyl group; aryl groups such as a phenyl group, a tolyl group, and a xylyl group; aralkyl groups such as a benzyl group and a phenethyl group; and halogenated alkyl groups such as a 3-chloropropyl group and a 3,3,3-trifluoropropyl group. A methyl group and a phenyl group are preferred. The viscosity at 25° C. of component (B) is not particularly limited, and is preferably in the range of from 1 to 10,000 mPa·s, and particularly preferably in the range of from 1 to 1,000 mPa·s.

Examples of such an organohydrogenpolysiloxane for component (B) include 1,1,3,3-tetramethyldisiloxane, 1,3,5,7-tetramethylcyclotetrasiloxane, tris(dimethylhydrogensiloxy)methylsilane, tris(dimethylhydrogensiloxy)phenylsilane, 1-glycidoxypropyl-1,3,5,7-tetramethylcyclotetrasiloxane, 1,5-diglycidoxypropyl-1,3,5,7-tetramethylcyclotetrasiloxane, 1-glycidoxypropyl-5-trimethoxysilylethyl-1,3,5,7-tetramethylcyclotetrasiloxane, a methylhydrogenpolysiloxane having both molecular terminals capped with trimethylsiloxy groups, a dimethylsiloxane-methylhydrogensiloxane copolymer having both molecular terminals capped with trimethylsiloxy groups, a dimethylpolysiloxane having both molecular terminals capped with dimethylhydrogensiloxy groups, a dimethylsiloxane-methylhydrogensiloxane copolymer having both molecular terminals capped with dimethylhydrogensiloxy groups, a methylhydrogensiloxane-diphenylsiloxane copolymer having both molecular terminals capped with trimethylsiloxy groups, a methylhydrogensiloxane-diphenylsiloxane-dimethylsiloxane copolymer having both molecular terminals capped with trimethylsiloxy groups, a hydrolysis-condensation product of trimethoxysilane, a copolymer including a $(CH_3)_2HSiO_{1/2}$ unit and an $SiO_{4/2}$ unit, a copolymer including a $(CH_3)_2HSiO_{1/2}$ unit, an $SiO_{4/2}$ unit, and a $(C_6H_5)SiO_{3/2}$ unit, and the following organohydrogenpolysiloxanes. In the formulae, Me, Vi, Ph, and NapH represent a methyl group, a vinyl group, a phenyl group, and a naphthyl group, respectively, y and y' are each an integer of from 1 to 100, and c, d, e, and f are positive numbers, provided that the sum of c, d, e, and f in the molecule is 1.

$HMe_2SiO(Ph_2SiO)_ySiMe_2H$
$HMePhSiO(Ph_2SiO)_ySiMePhH$
$HMeNaphSiO(Ph_2SiO)_ySiMeNaphH$
$HMePhSiO(Ph_2SiO)_y(MePhSiO)_{y'}SiMePhH$
$HMePhSiO(Ph_2SiO)_y(Me_2SiO)_{y'}SiMePhH$
$(HMe_2SiO_{1/2})_c(PhSiO_{3/2})_d$
$(HMePhSiO_{1/2})_c(PhSiO_{3/2})_d$
$(HMePhSiO_{1/2})_c(NaphSiO_{3/2})_d$
$(HMe_2SiO_{1/2})_c(NaphSiO_{3/2})_d$
$(HMePhSiO_{1/2})_c(HMe_2SiO_{1/2})_d(PhSiO_{3/2})_e$
$(HMe_2SiO_{1/2})_c(Ph_2SiO_{2/2})_d(PhSiO_{3/2})_e$
$(HMePhSiO_{1/2})_c(Ph_2SiO_{2/2})_d(PhSiO_{3/2})_e$
$(HMe_2SiO_{1/2})_c(Ph_2SiO_{2/2})_d(NaphSiO_{3/2})_e$
$(HMePhSiO_{1/2})_c(Ph_2SiO_{2/2})_d(NaphSiO_{3/2})_e$
$(HMePhSiO_{1/2})_c(HMe_2SiO_{1/2})_d(NaphSiO_{3/2})_e$
$(HMePhSiO_{1/2})_c(HMe_2SiO_{1/2})_d(Ph_2SiO_{2/2})_e(NaphSiO_{3/2})_f$
$(HMePhSiO_{1/2})_c(HMe_2SiO_{1/2})_d(Ph_2SiO_{2/2})_e(PhSiO_{3/2})_f$ The content of component (B) is an amount such that the silicon atom-bonded hydrogen atoms in component (B) is in the range of from 0.1 to 10.0 mol, and preferably in the range of from 0.5 to 5 mol, relative to 1 mol of all the alkenyl groups in components (A) and (C). When the content of component (B) is less than or equal to the upper limit of the aforementioned range, the mechanical characteristics of a cured product to be obtained is good. In contrast, when the content of component (B) is greater than or equal to the lower limit of the range, the curability of the obtained composition is good.

Component (C) is an adhesion promoter for imparting adhesion to the present composition. Component (C) is as described above. The content of component (C) is in the range of from 0.01 to 50 parts by mass, and preferably in the range of from 0.1 to 25 parts by mass, relative to 100 parts by mass of component (A). When the content of component (C) is greater than or equal to the lower limit of the aforementioned range, sufficient adhesion can be imparted to the obtained composition. In contrast, when the content of component (C) is less than or equal to the upper limit of the range, the curability of the obtained composition is unlikely to be inhibited, and coloring of the cured product to be obtained, and the like can be suppressed.

Component (D) is a hydrosilylation reaction catalyst for accelerating the curing of the present composition, and examples thereof include platinum-based catalysts, rhodium-based catalysts, and palladium-based catalysts. Particularly, component (D) is preferably a platinum-based catalyst since the curing of the present composition can be dramatically accelerated. Examples of the platinum-based catalyst include a platinum fine powder, chloroplatinic acid, an alcohol solution of chloroplatinic acid, a platinum-alkenylsiloxane complex, a platinum-olefin complex, and a platinum-carbonyl complex, and a platinum-alkenylsiloxane complex is preferred.

The content of component (D) is an effective amount for accelerating the curing of the composition. Specifically, in order to be able to sufficiently accelerate the curing reaction of the composition, the content of component (D) is preferably an amount such that the catalyst metal in component (D) is in the range of 0.01 to 500 ppm, more preferably in the range of 0.01 to 100 ppm, and particularly preferably in the range of 0.01 to 50 ppm in mass units with respect to this composition.

This composition may contain a reaction inhibitor, for example, an alkyne alcohol such as 2-methyl-3-butyn-2-ol, 3,5-dimethyl-1-hexyn-3-ol, and 2-phenyl-3-butyn-2-ol; an ene-yne compound such as 3-methyl-3-penten-1-yne, and 3,5-dimethyl-3-hexen-1-yne; or 1,3,5,7-tetramethyl-1,3,5,7-tetravinylcyclotetrasiloxane, 1,3,5,7-tetramethyl-1,3,5,7-tetrahexenylcyclotetrasiloxane, or a benzotriazole, as an optional component. The content of the reaction inhibitor in the composition is not particularly limited, and is preferably in the range of from 0.0001 to 5 parts by mass relative to the total of 100 parts by mass of components (A) to (C).

The present composition may contain an adhesion promoter other than component (C) in order to improve the adhesion of the cured product to a base material in contact with the cured product during the curing. It is preferable that this adhesion promoter be an organosilicon compound having at least one alkoxy group bonded to a silicon atom in a molecule. Examples of this alkoxy group include a methoxy group, an ethoxy group, a propoxy group, a butoxy group, and a methoxyethoxy group, and a methoxy group is particularly preferred. Moreover, examples of a group bonded to a silicon atom of this organosilicon compound, except for an alkoxy group, include substituted or unsubstituted monovalent hydrocarbon groups such as alkyl groups, alkenyl groups, aryl groups, aralkyl groups, halogenated alkyl groups, and the like; epoxy group-containing monovalent organic groups such as a 3-glycidoxypropyl group, a 4-glycidoxybutyl group, or similar glycidoxyalkyl groups, a 2-(3,4-epoxycyclohexyl)ethyl group, a 3-(3,4-epoxycyclohexyl) propyl group, or similar epoxycyclohexylalkyl groups, and a 4-oxiranylbutyl group, an 8-oxiranyloctyl group, or similar oxiranylalkyl groups; acrylic group-containing monovalent organic groups such as a 3-methacryloxypropyl group; and a hydrogen atom. This organosilicon compound preferably has a silicon atom-bonded alkenyl group or silicon atom-bonded hydrogen atom. Moreover, since good adhesion can be imparted to various types of base materials, this organosilicon compound preferably has at least one epoxy group-containing monovalent organic group in a molecule. Examples of such an organosilicon compound include organosilane compounds, organosiloxane oligomers, and alkyl silicates. Examples of the molecular structure of the organosiloxane oligomer or alkyl silicate include linear, partially branched linear, branched, cyclic, and net-shaped structures. It is preferable that the molecular structure be a linear, branched, or net-shaped structure. Examples of this type of organosilicon compound include silane compounds such as 3-glycidoxypropyl trimethoxysilane, 2-(3,4-epoxycyclohexyl)ethyl trimethoxysilane, and 3-methacryloxypropyl trimethoxysilane; siloxane compounds having at least one of silicon atom-bonded alkenyl groups and silicon atom-bonded hydrogen atoms, and at least one silicon atom-bonded alkoxy group in a molecule; mixtures of a silane compound or siloxane compound having at least one silicon atom-bonded alkoxy group and a siloxane compound having at least one silicon atom-bonded hydroxyl group and at least one silicon atom-bonded alkenyl group in a molecule; methyl polysilicate, ethyl polysilicate, and epoxy group-containing ethyl polysilicate.

The present composition may contain a phosphor for obtaining a light with a desired wavelength by altering the wavelength of light emitted from a light emitting element that is encapsulated or covered with the cured product of the present composition. Examples of this type of phosphor include yellow, red, green, and blue light emitting phosphors such as oxide phosphors, oxynitride phosphors, nitride phosphors, sulfide phosphors, and oxysulfide phosphors, which are widely used in light emitting diodes (LEDs). Examples of oxide phosphors include yttrium, aluminum, and garnet-type YAG green to yellow light emitting phosphors containing cerium ions; terbium, aluminum, and garnet-type TAG yellow light emitting phosphors containing cerium ions; and silicate green to yellow light emitting phosphors containing cerium or europium ions. Examples of oxynitride phosphors include silicon, aluminum, oxygen, and nitrogen-type SiAlON red to green light emitting phosphors containing europium ions. Examples of nitride-based phosphors include calcium, strontium, aluminum, silicon, and nitrogen-type CASN red light emitting phosphors containing europium ions. Examples of sulfide phosphors include ZnS green light emitting phosphors containing copper ions or aluminum ions. Examples of oxysulfide phosphors include $Y_2O_2S$ red light emitting phosphors containing europium ions. These fluorescent substances may be used as one type or as a mixture of two or more types. In the present composition, the content of the phosphor is in the range of from 0.1 to 70 mass %, and preferably in the range of from 1 to 20 mass %, relative to the total amount of components (A) and (B).

Moreover, the present composition may contain an inorganic filler such as silica, glass, alumina, zinc oxide, or the like; an organic resin fine powder of a polymethacrylate resin or the like; a heat-resistant agent, a dye, a pigment, a flame retardant, a solvent, or the like as an optional component as long as the object of the present invention is not impaired.

Of components added as the optional component, in order to sufficiently suppress discoloration of silver electrodes or silver plating of a substrate in an optical semiconductor device due to sulfur-containing gas in the air, it is possible to add at least one type of a fine powder having an average particle diameter of from 0.1 nm to 5 μm selected from the group consisting of zinc oxide fine powders surface-coated with at least one type of oxide of an element selected from the group consisting of Al, Ag, Cu, Fe, Sb, Si, Sn, Ti, Zr, and rare earth elements, zinc oxide fine powders surface-treated with organosilicon compounds not having alkenyl groups, and hydrate fine powders of zinc carbonate.

In a zinc oxide fine powder surface-coated with an oxide, examples of rare earth elements include yttrium, cerium, and europium. Examples of the oxide on the surface of the zinc oxide fine powder include $Al_2O_3$, AgO, $Ag_2O$, $Ag_2O_3$, CuO, $Cu_2O$, FeO, $Fe_2O_3$, $Fe_3O_4$, $Sb_2O_3$, $SiO_2$, $SnO_2$, $Ti_2O_3$, $TiO_2$, $Ti_3O_5$, $ZrO_2$, $Y_2O_3$, $CeO_2$, $Eu_2O_3$, and a mixture of two or more types thereof.

In a zinc oxide powder surface-treated with an organic silicon compound, the organic silicon compound does not have alkenyl groups, and examples include organosilanes, organosilazanes, polymethylsiloxanes, organohydrogenpolysiloxanes, and organosiloxane oligomers. Specific examples include organochlorosilanes such as trimethylchlorosilane, dimethylchlorosilane, and methyltrichlorosilane; organotrialkoxysilanes such as methyltrimethoxysilane, methyltriethoxysilane, phenyltrimethoxysilane, ethyltrimethoxysilane, n-propyltrimethoxysilane, and γ-methacryloxypropyltrimethoxysilane; diorganodialkoxysilanes such as dimethyldimethoxysilane, dimethyldiethoxysilane, and diphenyldimethoxysilane; triorganoalkoxysilanes such as trimethylmethoxysilane and trimethylethoxysilane; partial condensates of these organoalkoxysilanes; organosilazanes such as hexamethyldisilazane; and resin-like organopolysiloxanes consisting of a polymethylsiloxane, an organohydrogenpolysiloxane, an organosiloxane oligomer having a silanol group or an alkoxy group, an $R^6SiO_{3/2}$ unit (wherein $R^6$ is a monovalent hydrocarbon group excluding alkenyl groups, examples of which include alkyl groups such as a methyl group, an ethyl group, or a propyl group; and aryl groups such as a phenyl group), or an $SiO_{4/2}$ unit.

In addition, the composition may also contain a triazole-based compound as an optional component since discoloration of the silver electrodes or the silver plating of the substrate due to a sulfur-containing gas in the air can be further suppressed. Examples of such components include 1H-1,2,3-triazole, 2H-1,2,3-triazole, 1H-1,2,4-triazole, 4H-1,2,4-triazole, 2-(2'-hydroxy-5'-methylphenyl)benzotriazole, 1H-1,2,3-triazole, 2H-1,2,3-triazole, 1H-1,2,4-triazole, 4H-1,2,4-triazole, benzotriazole, tolyltriazole, carboxybenzotriazole, 1H-benzotriazole-5-methyl carboxylate, 3-amino-1,2,4-triazole, 4-amino-1,2,4-triazole, 5-amino-1,2,4-triazole, 3-mercapto-1,2,4-triazole, chlorobenzotriazole, nitrobenzotriazole, aminobenzotriazole, cyclohexano[1,2-d]triazole, 4,5,6,7-tetrahydroxytolyltriazole, 1-hydroxybenzotriazole, ethylbenzotriazole, naphthotriazole, 1-N,N-bis(2-ethylhexyl)-[(1,2,4-triazole-1-yl)methyl]amine, 1-[N,N-bis(2-ethylhexyl)aminomethyl]benzotriazole, 1-[N,N-bis(2-ethylhexyl)aminomethyl]tolyltriazole, 1-[N,N-bis(2-ethylhexyl)aminomethyl]carboxybenzotriazole, 1-[N,N-bis(2-hydroxyethyl)-aminomethyl]benzotriazole, 1-[N,N-bis(2-hydroxyethyl)-aminomethyl]tolyltriazole, 1-[N,N-bis(2-hydroxyethyl)-aminomethyl]carboxybenzotriazole, 1-[N,N-bis(2-hydroxypropyl)aminomethyl]carboxybenzotriazole, 1-[N,N-bis(1-butyl)aminomethyl]carboxybenzotriazole, 1-[N,N-bis(1-octyl)aminomethyl]carboxybenzotriazole, 1-(2',3'-di-hydroxypropyl)benzotriazole, 1-(2',3'-di-carboxyethyl)benzotriazole, 2-(2'-hydroxy-3',5'-di-tert-butylphenyl)benzotriazole, 2-(2'-hydroxy-3',5'-amylphenyl)benzotriazole, 2-(2'-hydroxy-4'-octoxyphenyl)benzotriazole, 2-(2'-hydroxy-5'-tert-butylphenyl)benzotriazole, 1-hydroxybenzotriazole-6-carboxylic acid, 1-oleoylbenzotriazole, 1,2,4-triazol-3-ol, 5-amino-3-mercapto-1,2,4-triazole, 5-amino-1,2,4-triazole-3-carboxylic acid, 1,2,4-triazole-3-carboxyamide, 4-aminourazole, and 1,2,4-triazol-5-one. The content of this benzotriazole compound is not particularly limited, and is an amount in the range of from 0.01 ppm to 3%, and preferably in the range of from 0.1 ppm to 1% of the composition in terms of mass units.

The present composition is cured either at room temperature or under heating, but it is preferable to heat the composition in order to achieve rapid curing. The heating temperature is preferably in the range of from 50 to 200° C.

The semiconductor device of the present invention will now be described in detail. The semiconductor device of the present invention is by encapsulating a semiconductor element with the cured product of the curable silicone composition described above. Examples of such a semiconductor device of the present invention include a light emitting diode (LED), a photocoupler, and a CCD. Examples of the semiconductor element include a light emitting diode (LED) chip and a solid-state image sensing device.

FIG. 1 illustrates a cross-sectional view of a single surface mounted type LED, which is one example of the semiconductor device of the present invention. In the LED illustrated in FIG. 1, a light emitting element (LED chip) 1 is die-bonded to a lead frame 2, and the light emitting element (LED chip) 1 and a lead frame 3 are wire-bonded by a bonding wire 4. A frame material 5 is provided around the periphery of this light emitting element (LED chip) 1, and the light emitting element (LED chip) 1 on the inner side of this frame material 5 is encapsulated with a cured product 6 of the curable silicone composition of the present invention.

An example of a method for producing the surface mounted type LED illustrated in FIG. 1 is a method comprising die-bonding the light emitting element (LED chip) 1 to the lead frame 2, wire-bonding this light emitting element (LED chip) 1 and the lead frame 3 by means of a metal bonding wire 4, charging the inside of the frame material 5 provided around the periphery of the light emitting element (LED chip) 1 with the curable silicone composition of the present invention, and then curing the curable silicone composition by heating to 50 to 200° C.

EXAMPLES

The organosilicon compound, the curable silicone composition, and the semiconductor device of the present invention will be described in detail hereinafter using Examples. In the formulae, Me, Vi, Ph, and Ep represent a methyl group, a vinyl group, a phenyl group, and a 3-glycidoxypropyl group, respectively.

Reference Example 1

First, 400 g (2.02 mol) of phenyltrimethoxysilane and 93.5 g (0.30 mol) of 1,3-divinyl-1,3-diphenyldimethyldisiloxane were loaded in a reaction vessel and mixed in advance. Next, 1.74 g (11.6 mmol) of trifluoromethane sulfonic acid was added, and 110 g (6.1 mol) of water was added and heat-refluxed for 2 hours while stirring. The mixture was then distilled at atmospheric pressure by heating until the temperature reached 85° C. Subsequently, 89 g of toluene and 1.18 g (21.1 mmol) of potassium hydroxide were added, and the mixture was distilled at atmospheric pressure by heating until the reaction temperature reached 120° C. and then allowed to react at this temperature for 6 hours. The mixture was then cooled to room temperature, and neutralized by adding 0.68 g (11.4 mmol) of acetic acid. The produced salt was filtered off to obtain a transparent solution. From the transparent solution, a low boiling point substance was removed by heating under reduced pressure, to obtain 347 g (yield: 98%) of organopolysiloxane resin represented by the average unit formula:

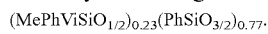
(MePhViSiO$_{1/2}$)$_{0.23}$(PhSiO$_{3/2}$)$_{0.77}$.

Example 1

In a reaction vessel, 30 g of cyclic methylvinylsiloxane and 0.011 g of solution of platinum-1,3-divinyl-1,1,3,3-tetramethyldisiloxane complex in toluene were charged and heated to 100° C. Subsequently, 21.5 g of disiloxane represented by the formula:

[Chemical Formula 22]

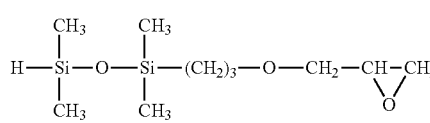

was added dropwise. After completion of dropwise addition, a reaction was carried out for 2 hours. By analysis of IR spectroscopy, it was confirmed that the reaction mixture did not contain silicon atom-bonded hydrogen atoms. Next, a low-boiling component was removed under reduced pressure to obtain a light yellow liquid. This liquid was analyzed by $^{29}$Si-NMR. As a result, signals appeared at about –32 ppm, about –18.4 ppm, and about 7.9 to 9 ppm. It was confirmed that the liquid was an organosilicon compound represented by the average formula:

[Chemical Formula 23]

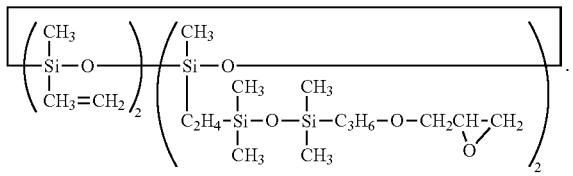

Example 2

In a reaction vessel, 20 g of cyclic methylvinylsiloxane and 0.013 g of solution of platinum-1,3-divinyl-1,1,3,3-tetramethyldisiloxane complex in toluene were charged and heated to 100° C. Next, a mixture of 14.4 g (0.058 mol) of disiloxane represented by the formula:

[Chemical Formula 24]

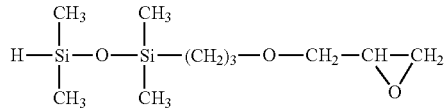

and 17.2 g (0.058 mol) of disiloxane represented by the formula:

[Chemical Formula 25]

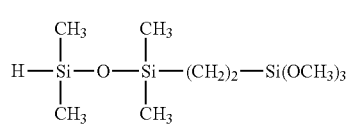

were added dropwise. After completion of dropwise addition, the mixture was heated for 2 hours. By IR spectroscopy, it was confirmed that the reaction mixture did not contain silicon atom-bonded hydrogen atoms. Next, a low-boiling component was removed under reduced pressure to obtain a light yellow liquid. This liquid was analyzed by $^{29}$Si-NMR. As a result, signals appeared at about –42 ppm, –32 ppm, about –18.4 ppm, and about 7.3 to 8.7 ppm. It was confirmed that the liquid was an organosilicon compound represented by the average formula:

[Chemical Formula 26]

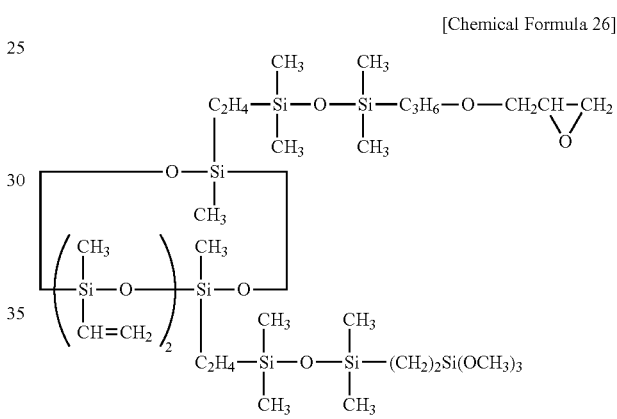

Example 3

In a reaction vessel, 15 g of cyclic methylvinylsiloxane and 0.01 g of solution of platinum-1,3-divinyl-1,1,3,3-tetramethyldisiloxane complex in toluene were charged and heated to 100° C. Subsequently, 25.8 g (0.087 mol) of disiloxane represented by the formula:

[Chemical Formula 27]

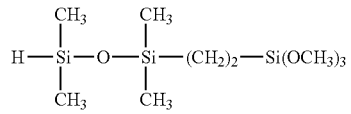

was added dropwise. After completion of dropwise addition, the mixture was heated for 2 hours. By IR spectroscopy, it was confirmed that the reaction mixture did not contain silicon atom-bonded hydrogen atoms. Next, a low-boiling component was removed under reduced pressure to obtain a light yellow liquid. This liquid was analyzed by $^{29}$Si-NMR. As a result, signals appeared at about –42 ppm, –32 ppm, about –18.4 ppm, and about 7.1 to 8.5 ppm. It was confirmed that the liquid was an organosilicon compound represented by the average formula:

[Chemical Formula 28]

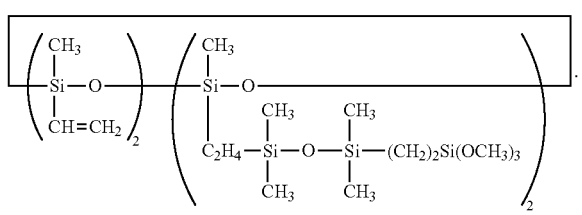

Example 4

In a reaction vessel, 30 g of tetrakisvinyldimethylsiloxy silane and 0.01 g of solution of platinum-1,3-divinyl-1,1,3,3-tetramethyldisiloxane complex in toluene were charged and heated to 80° C. Next, a mixture of 16.9 g (0.068 mol) of disiloxane represented by the formula:

[Chemical Formula 29]

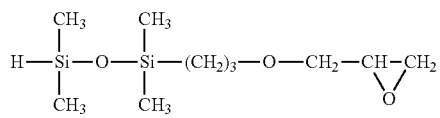

and 20.2 g (0.068 mol) of disiloxane represented by the formula:

[Chemical Formula 30]

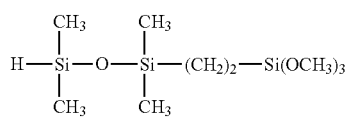

were added dropwise. After completion of dropwise addition, the mixture was heated for 2 hours. By IR spectroscopy, it was confirmed that the reaction mixture did not contain silicon atom-bonded hydrogen atoms. Next, a low-boiling component was removed under reduced pressure to obtain a light yellow liquid. This liquid was analyzed by $^{29}$Si-NMR. As a result, signals appeared at −104 ppm, about −42 ppm, −32 ppm, about −2.6 ppm, and about 7.1 to 8.7 ppm. It was confirmed that the liquid was an organosilicon compound represented by the average formula:

[Chemical Formula 31]

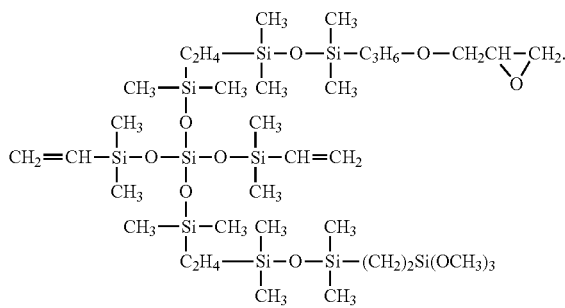

Reference Example 1

47.7 g (0.418 mol) of allyl glycidyl ether was added dropwise to a mixed solution of 50 g (0.835 mol) of cyclic methylhydrogensiloxane and 9.8 µL of solution of platinum-1,3-divinyl-1,1,3,3-tetramethyldisiloxane complex in toluene at 70° C. After completion of dropwise addition, the mixture was heated for 2 hours. By gas chromatography, it was confirmed that the reaction mixture did not contain allyl glycidyl ether. Next, a low-boiling component was removed under reduced pressure to obtain a transparent liquid. This liquid was analyzed by $^{29}$Si-NMR. As a result, signals appeared at −32.9 ppm and about −17.7 to −16.2 ppm. It was confirmed that the liquid is an organosiloxane represented by the average formula:

[Chemical Formula 32]

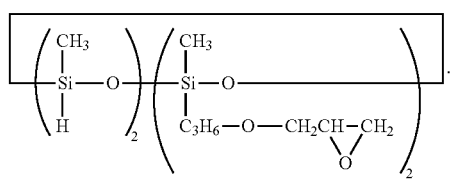

Examples 5 to 10 and Comparative Examples 1 to 3

A curable silicone composition having each composition shown in Table 1 was prepared using the following components. In Table 1, the content of component (D) is expressed in terms of the content (ppm) of platinum metal relative to the curable silicone composition in terms of mass units. Note that the H/Vi values in Table 1 refer to the number of moles of silicon atom-bonded hydrogen atoms contained in component (B), relative to 1 mole of alkenyl groups contained in components (A) and (C).

The following components were used as component (A).
Component (A-1): organopolysiloxane represented by the average unit formula:

(Me$_2$ViSiO$_{1/2}$)$_{0.2}$(PhSiO$_{3/2}$)$_{0.8}$ (content of vinyl group=4.1 mass %)
Component (A-2): organopolysiloxane represented by the average unit formula:

(MePhViSiO$_{1/2}$)$_{0.23}$(PhSiO$_{3/2}$)$_{0.77}$ (content of vinyl group=4.59 mass %)
Component (A-3): methylphenylpolysiloxane having both molecular terminals capped with dimethylvinylsiloxy groups, having viscosity of 3,000 mPa·s at 25° C. (content of vinyl group=1.8 mass %)

The following components were used as component (B).
Component (B-1): organotrisiloxane represented by the formula:

HMe$_2$SiOPh$_2$SiOSiMe$_2$H

The following components were used as component (C).
Component (C-1): adhesion promoter prepared in Example 1
Component (C-2): adhesion promoter prepared in Example 2
Component (C-3): adhesion promoter prepared in Example 3

Component (C-4): adhesion promoter prepared in Example 4

Component (C-5): adhesion-imparting agent including a condensation reaction product of a methylvinylsiloxane oligomer having both molecular terminals capped with silanol groups and having a viscosity at 25° C. of 30 mPa·s, and and 3-glycidoxypropyltrimethoxysilane (content of vinyl group=5.6 mass %) Componen (C-6): adhesion promoter represented by the formula:

[Chemical Formula 33]

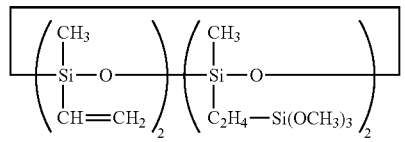

Component (C-7): adhesion promoter prepared in Reference Example 1

The following components were used as component (D).

Component (D-1): solution of platinum-1,3-divinyl-1,1,3,3-tetramethyldisiloxane complex in 1,3,5,7-tetramethyl-1,3,5,7-tetravinylcyclotetrasiloxane (the solution contains 0.1 mass % of platinum)

Cured products of curable silicone compositions and semiconductor devices were evaluated as follows.

Adhesion Force of Cured Product of Curable Silicone Composition

A spacer made of a polytetrafluoroethylene resin (width: 10 mm, length: 20 mm, thickness: 1 mm) was placed between two aluminum plates, silver plates, or polyphthalamide plates (width: 25 mm, length: 75 mm, thickness: 1 mm), a gap between the plates was filled with a curable silicone composition, and the plates were clipped and held in a circulating hot air oven of 150° C. for 1 hour. Thus, the curable silicone composition was cured. After cooling to room temperature, the clip and the spacer were taken out. The stress during breakage was measured by drawing the aluminum plates in horizontal and opposite directions by a tension tester.

Production of Surface Mounted Type Light Emitting Diode (LED)

In a cylindrical frame 5 that was made from polyphthalamide (PPA) resin and that had a closed bottom (inner diameter: 2.0 mm; depth: 1.0 mm), lead frames 2 and 3 were extended from side walls of the frame 5 toward the center of inner bottom of the frame 5. An LED chip 1 was mounted on the central part of the lead frame 2, and the LED chip 1 and the lead frame 3 were electrically connected by a bonding wire 4 in an unsealed light emitting diode. The curable silicone composition was degassed and injected into the unencapsulated semiconductor device by a dispenser. Subsequently, the semiconductor device was held at a first curing temperature (70° C.) for 1 hour and then a second curing temperature (150° C.) for 1 hour, to cure the curable silicone composition. Thus, a surface mounted type light emitting diode (LED) illustrated in FIG. 1 was produced.

Ink Test 16 light emitting diodes produced by the method described above were immersed in a commercially available red ink, and left at 50° C. for 24 hours. After the light emitting diodes were left, the immersion of the red ink was checked by a microscope, and evaluated as follows.

⊚: Immersion of the ink was observed in two or less light emitting diodes.

Δ: Immersion of the ink was observed in three to eight light emitting diodes.

x: Immersion of the ink was observed in nine or more light emitting diodes.

Wire Breakage 16 light emitting diodes produced by the method described above were left while a cycle of changing the temperature between −40° C. and 125° C. for 1 hour was repeated 1,000 times. Lighting of LED was checked by applying current, and evaluated as follows.

⊚: Fourteen or more light emitting diodes were lighted up.

○: Eight to thirteen light emitting diodes were lighted up.

Δ: Seven or less light emitting diodes were lighted up.

TABLE 1

|  |  | Present invention | | | | |
| --- | --- | --- | --- | --- | --- | --- |
|  |  | Example 5 | Example 6 | Example 7 | Example 8 | Example 9 |
| Composition of curable silicone composition (part by mass) | Component (A-1) | 60 | 60 | 60 | 60 | — |
|  | Component (A-2) | — | — | — | — | 53 |
|  | Component (A-3) | 15 | 15 | 15 | 15 | 23 |
|  | Component (B-1) | 17.9 | 17.9 | 17.9 | 17.9 | 16 |
|  | Component (C-1) | 0.5 | — | — | — | — |
|  | Component (C-2) | — | 0.5 | — | — | 0.5 |
|  | Component (C-3) | — | — | 0.5 | — | — |
|  | Component (C-4) | — | — | — | 0.5 | — |
|  | Component (C-5) | — | — | — | — | — |
|  | Component (C-6) | — | — | — | — | — |
|  | Component (C-7) | — | — | — | — | — |
|  | Component (D-1) | 2.5 ppm | 2.5 ppm | 2.5 ppm | 2.5 ppm | 5 ppm |
| H/Vi |  | 1.0 | 1.0 | 1.0 | 1.0 | 0.9 |
| Adhesion (MPa) |  |  |  |  |  |  |
| Aluminum plate |  | 10 | 10 | 8 | 7 | 9 |
| PPA resin plate |  | 7.5 | 8 | 7.5 | 7 | 8 |
| Silver plate |  | 6.5 | 6.5 | 5 | 7 | 8 |
| Ink test |  | ⊚ | ⊚ | ⊚ | ⊚ | ⊚ |
| Wire breakage |  | ⊚ | ⊚ | ○ | ⊚ | ⊚ |

TABLE 1-continued

|  |  | Comparative Examples | | | | |
|---|---|---|---|---|---|---|
|  |  | Comp. Example 1 | Comp. Example 2 | Comp. Example 3 | Comp. Example 4 | Comp. Example 5 |
| Composition of curable silicone composition (part by mass) | Component (A-1) | 60 | 60 | 60 | — | 60 |
|  | Component (A-2) | — | — | — | 53 | — |
|  | Component (A-3) | 15 | 15 | 15 | 23 | 15 |
|  | Component (B-1) | 17.9 | 17.9 | 17.9 | 16 | 17 |
|  | Component (C-1) | — | — | — | — | — |
|  | Component (C-2) | — | — | — | — | — |
|  | Component (C-3) | — | — | — | — | — |
|  | Component (C-4) | — | — | — | — | — |
|  | Component (C-5) | 0.5 | — | — | 0.5 | — |
|  | Component (C-6) | — | 0.5 | — | — | — |
|  | Component (C-7) | — | — | — | — | 0.5 |
|  | Component (D-1) | 2.5 ppm | 2.5 ppm | 2.5 ppm | 5 ppm | 2.5 ppm |
| H/Vi |  | 1.0 | 1.0 | 1.0 | 0.9 | 1.0 |
| Adhesion (MPa) |  |  |  |  |  |  |
| Aluminum plate |  | 6 | 5 | X | 6 | 5.0 |
| PPA resin plate |  | 5 | 4 | X | 5 | 6.0 |
| Silver plate |  | 5 | 4 | 3 | 5 | 4.9 |
| Ink test |  | Δ | Δ | X | Δ | Δ |
| Wire breakage |  | Δ | Δ | ⊚ | Δ | — |

Examples 10 and 11 and Comparative Example 6

The following components were uniformly mixed according to the compositions shown in Table 2 to prepare curable silicone compositions of Examples 10 and 11 and Comparative Example 6. In Table 2, the content of component (D) is expressed in terms of the content (ppm) of platinum metal relative to each of the curable silicone compositions in terms of mass units. Note that H/Vi in Table 2 refer to the number of moles of silicon atom-bonded hydrogen atoms contained in component (B), relative to 1 mol of alkenyl groups contained in components (A) and (C).

The following components were used as component (A).

Component (A-4): organopolysiloxane having a viscosity at 25° C. of 10,000 mPa·s and represented by the average formula:

$Me_2ViSiO(Me_2SiO)_{500}SiMe_2Vi$ (content of vinyl group=0.15 wt. %)

Component (A-5): organopolysiloxane being a white solid at 25° C., soluble in toluene, having two or more vinyl groups in a molecule, and represented by the average unit formula:

$(Me_2ViSiO_{1/2})_{0.10}(Me_3SiO_{1/2})_{0.40}(SiO_{4/2})_{0.50}$
$(HO_{1/2})_{0.0001}$ (content of vinyl group=3.39 mass %)

Component (A-6): organopolysiloxane having a viscosity of 300 mPa·s and represented by the average formula:

$Me_2ViSiO(Me_2SiO)_{150}SiMe_2Vi$ (content of vinyl group=0.48 wt. %)

Component (A-7): organopolysiloxane resin being a white solid at 25° C., soluble in toluene, having two or more vinyl groups in a molecule, and represented by the average unit formula:

$(Me_2ViSiO_{1/2})_{0.06}(Me_3SiO_{1/2})_{0.44}(SiO_{4/2})_{0.50}$
$(HO_{1/2})_{0.0001}$ (content of vinyl group=5.4 mass %)

Component (A-8): organopolysiloxane represented by the average formula:

$Me_2ViSiO(Me_2SiO)_{300}SiMe_2Vi$ (content of vinyl group=0.24 wt. %)

The following components were used as component (B).

Component (B-3): polymethylhydrogensiloxane having a viscosity at 25° C. of 5 mPa·s, having both molecular terminals capped with trimethylsiloxy groups, and represented by the average formula:

$Me_3SiO(MeHSiO)_mSiMe_3$ (content of silicon atom-bonded hydrogen atom=1.4 mass %)

Components (C-2), (C-3), and (C-5) described above were used as component (C).

Component (D-1) was used as component (D).

The following component was used as a reaction inhibitor.

Component (E-1): 1-ethynylcyclohexanol

Adhesion Force of Cured Product of Curable Silicone Composition

A spacer made of a polytetrafluoroethylene resin (width: 10 mm, length: 20 mm, thickness: 1 mm) was placed between two aluminum plates, silver plates, or polyphthalamide plates (width: 25 mm, length: 75 mm, thickness: 1 mm), a gap between the plates was filled with a curable silicone composition, and the plates were clipped and held in a circulating hot air oven of 150° C. for 1 hour. Thus, the curable silicone composition was cured. After cooling to room temperature, the clip and the spacer were taken out. The stress during breakage was measured by drawing the aluminum plates in horizontal and opposite directions by a tension tester.

TABLE 2

|  |  | Present invention | | Comparative |
|---|---|---|---|---|
|  |  | Example 10 | Example 11 | Comparative Example 6 |
| Composition of curable silicone composition (part by mass) | Component (A-4) | 18.2 | 18.2 | 18.2 |
|  | Component (A-5) | 22.1 | 22.1 | 22.1 |
|  | Component (A-6) | 13.6 | 13.6 | 13.6 |
|  | Component (A-7) | 23.2 | 23.2 | 23.2 |
|  | Component (A-8) | 18.1 | 18.1 | 18.1 |

TABLE 2-continued

|  | Present invention | | Comparative |
|---|---|---|---|
|  | Example 10 | Example 11 | Comparative Example 6 |
| Component (B-3) | 3.7 | 3.7 | 3.7 |
| Component (C-2) | 0.5 | — | — |
| Component (C-3) | — | 0.5 | — |
| Component (C-5) | — | — | 0.5 |
| Component (D-1)* | 5 ppm | 5 ppm | 5 ppm |
| Component (E-1)* | 0.06 | 0.06 | 0.06 |
| H/Vi | 1.1 | 1.1 | 1.1 |
| Adhesion force (MPa) | | | |
| Aluminum plate | 7 | 6 | 5 |
| Silver plate | 7 | 7 | 6 |

INDUSTRIAL APPLICABILITY

The curable silicone composition of the present invention has excellent fluidity, and a cured product in which phosphors are homogeneously dispersed and which has a high refractive index can be formed by curing the curable silicone composition. Therefore, the curable silicone composition is suitable for use as a sealing agent or coating agent for light emitting elements in optical semiconductor devices such as light emitting diodes (LEDs).

DESCRIPTION OF SYMBOLS

1 Light emitting element
2 Lead frame
3 Lead frame
4 Bonding wire
5 Frame material
6 Cured product of curable silicone composition

The invention claimed is:

1. An organosilicon compound represented by the general formula:

Chemical Formula 34

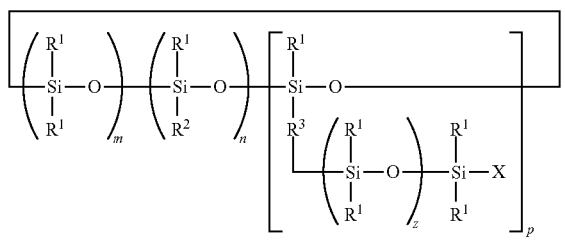

wherein, $R^1$ are the same or different monovalent hydrocarbon groups each having from 1 to 12 carbon atoms and no aliphatic unsaturated bond; $R^2$ is an alkenyl group having from 2 to 12 carbon atoms; $R^3$ is an alkylene group having 2 to 12 carbon atoms; X is at least one group selected from the group consisting of an alkoxysilylalkyl group, a glycidoxyalkyl group, an epoxycycloalkylalkyl group, an epoxyalkyl group, and a carboxylic acid anhydride residue-containing alkyl group; m is an integer of 0 or greater, n is an integer of 1 or greater, and p is an integer of 1 or greater, provided that the sum of m, n, and p is an integer of from 3 to 50; and z is an integer of from 1 to 50.

2. The organosilicon compound according to claim 1, wherein $R^3$ is an ethylene group or a propylene group.

3. The organosilicon compound according to claim 1, wherein X is an alkoxysilylalkyl group and/or a glycidoxyalkyl group.

4. The organosilicon compound according to claim 1, wherein z is an integer of from 1 to 5.

5. An organosilicon compound represented by the general formula:

Chemical Formula 35

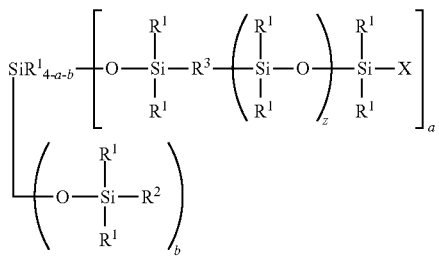

wherein, $R^1$ are the same or different monovalent hydrocarbon groups each having from 1 to 12 carbon atoms and no aliphatic unsaturated bond; $R^2$ is an alkenyl group having from 2 to 12 carbon atoms; $R^3$ is an alkylene group having from 2 to 12 carbon atoms; X is at least one group selected from the group consisting of an alkoxysilylalkyl group, a glycidoxyalkyl group, an epoxycycloalkylalkyl group, an epoxyalkyl group, and a carboxylic acid anhydride residue-containing alkyl group; a is an integer of from 1 to 3 and b is an integer of from 1 to 3, provided that the sum of a and b is an integer of from 2 to 4; and z is an integer of from 1 to 50.

6. The organosilicon compound according to claim 5, wherein $R^3$ is an ethylene group or a propylene group.

7. The organosilicon compound according to claim 5, wherein X is an alkoxysilylalkyl group and/or a glycidoxyalkyl group.

8. The organosilicon compound according to claim 5, wherein z is an integer of from 1 to 5.

9. An adhesion promoter comprising the organosilicon compound according to claim 1.

10. A curable silicone composition comprising the organosilicon compound according to claim 1 as an adhesion promoter.

11. The curable silicone composition according to claim 10 that is curable by a hydrosilylation reaction.

12. The curable silicone composition according to claim 11, wherein the hydrosilylation reaction curable silicone composition comprises:
    (A) 100 parts by mass of an organopolysiloxane having at least two alkenyl groups in a molecule;
    (B) an organohydrogenpolysiloxane having at least two silicon atom-bonded hydrogen atoms in a molecule, in an amount such that 0.1 to 10.0 mol of silicon atom-bonded hydrogen atom is provided relative to 1 mol of all alkenyl groups in components (A) and (C);
    (C) 0.01 to 50 parts by mass of adhesion promoter consisting of the organosilicon compound; and
    (D) a hydrosilylation reaction catalyst, in an amount sufficient to accelerate curing of the composition.

13. A semiconductor device comprising a semiconductor element sealed with a cured product of the curable silicone composition according to claim 10.

14. The semiconductor device according to claim 13, wherein the semiconductor element is a light emitting element.

15. An adhesion promoter comprising the organosilicon compound according to claim 5.

16. A curable silicone composition comprising the organosilicon compound according to claim 5 as an adhesion promoter.

17. The curable silicone composition according to claim 16 that is curable by a hydrosilylation reaction.

18. The curable silicone composition according to claim 17, wherein the hydrosilylation reaction curable silicone composition comprises:
 (A) 100 parts by mass of an organopolysiloxane having at least two alkenyl groups in a molecule;
 (B) an organohydrogenpolysiloxane having at least two silicon atom-bonded hydrogen atoms in a molecule, in an amount such that 0.1 to 10.0 mol of silicon atom-bonded hydrogen atom is provided relative to 1 mol of all alkenyl groups in components (A) and (C);
 (C) 0.01 to 50 parts by mass of adhesion promoter consisting of the organosilicon compound; and
 (D) a hydrosilylation reaction catalyst, in an amount sufficient to accelerate curing of the composition.

19. A semiconductor device comprising a semiconductor element sealed with a cured product of the curable silicone composition according to claim 16.

* * * * *